United States Patent [19]

Iannacchione et al.

[11] Patent Number: 4,468,973

[45] Date of Patent: Sep. 4, 1984

[54] REMOTE SEQUENTIAL GAS SAMPLER FOR BLASTING AREAS

[75] Inventors: Anthony T. Iannacchione, Pittsburg; David H. Lawhead, Avalon; John H. Perry, Scenery Hill, all of Pa.

[73] Assignee: The United States of America as represented by the Secretary of Interior, Washington, D.C.

[21] Appl. No.: 488,479

[22] Filed: Apr. 25, 1983

[51] Int. Cl.³ .......................... G01N 1/22; G01N 1/26
[52] U.S. Cl. ................................ 73/863.01; 73/864.63
[58] Field of Search ........................ 73/863.01, 864.63

[56] References Cited

U.S. PATENT DOCUMENTS

| | | | |
|---|---|---|---|
| 3,488,993 | 1/1970 | Raynor | 73/864.63 X |
| 4,037,472 | 7/1977 | Gates | 73/864.35 |
| 4,244,224 | 1/1981 | Conn | 73/863.23 |
| 4,300,384 | 11/1981 | Wiesner et al. | 73/863.01 X |
| 4,346,584 | 8/1982 | Boehringer | 73/863.02 X |

FOREIGN PATENT DOCUMENTS

| | | | |
|---|---|---|---|
| 443277 | 9/1974 | U.S.S.R. | 73/864.63 |
| 785667 | 12/1980 | U.S.S.R. | 73/864.63 |

*Primary Examiner*—S. Clement Swisher
*Assistant Examiner*—Tom Noland
*Attorney, Agent, or Firm*—Thomas Zack; Donald A. Gardiner

[57] ABSTRACT

A gas sampling device whose operation is activated by the blast whose gas is to be sampled. This blast activates a switch which in turn starts the operation box which thereafter sequentially outputs pneumatic signals at preset time intervals. These signals are received by a sampling unit assembly which functions in response thereto to receive and retain a gas sample from the blast.

5 Claims, 3 Drawing Figures

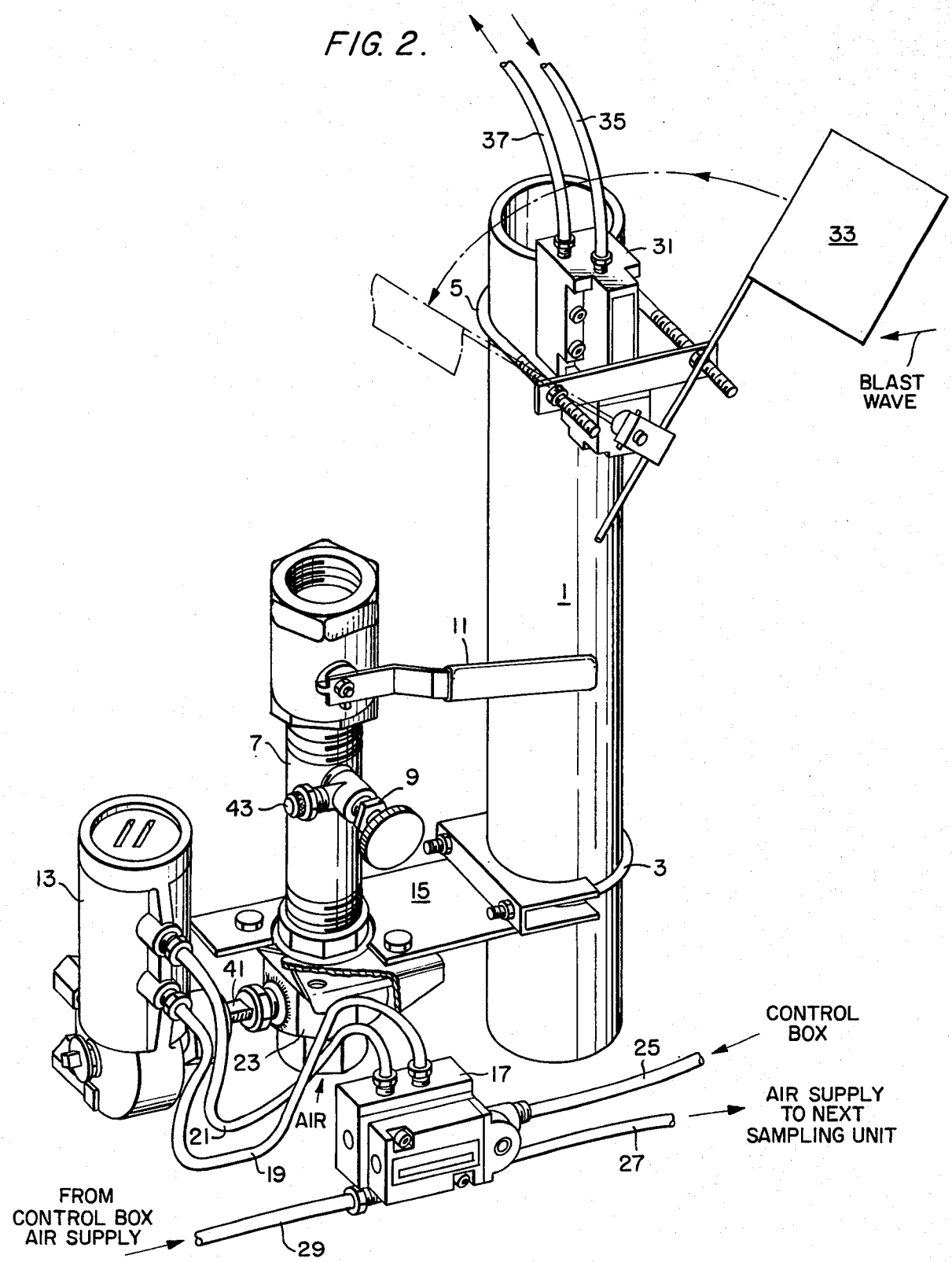

REMOTE SEQUENTIAL GAS SAMPLER FOR BLASTING AREAS

BACKGROUND OF THE INVENTION

The invention disclosed herein as a gas sampling device is especially designed and constructed to be used in a gassy underground mine environment.

DESCRIPTION OF THE PRIOR ART

The Mine Safety and Health Administration (MSHA) of the U.S. Department of Labor is the primary Federal Government agency concerned with setting the health and safety standards for miners in this country. Recently MSHA has classified many salt, oil shale, and trona mines as "gassy" since they have large methane gas emission problems. In particular, several salt mines in Louisiana have had serious methane emission problems associated with outbursts. These outbursts are known to occur only during the cutting or blasting of the salt.

In such gassy mines, MSHA requires all mine personnel to leave the mine before blasting takes place. This requirement, coupled with the knowledge that outbursts occur during the blasting operation have lead to the development of the gas sampling equipment constituting our invention. The subject matter of our invention is the only known equipment which complies with the MSHA permissibility requirements. It does this by providing an intrinsically safe, portable unit which is triggered by the pressure wave of the blast under investigation. In order to insure its instrinsic safety in the potentially explosive methane laden air, the sampler is pneumatically operated so as not to provide a spark.

SUMMARY OF THE INVENTION

An environmental gas sampling device used in underground gassy mines. The sampler is pneumatically operated by a pressure wave from the blast which triggers a timing sequence in an associated control box. Thereafter, at preset time intervals, pneumatic signals are sent to activate valves which provide for the capture of gas samples.

DESCRIPTION OF THE DRAWINGS

FIG. 2 illustrates the actuator unit and pneumatic gravity switch of FIG. 1 in more detail.

DESCRIPTION OF THE PREFERRED EMBODIMENT

Figure 1:
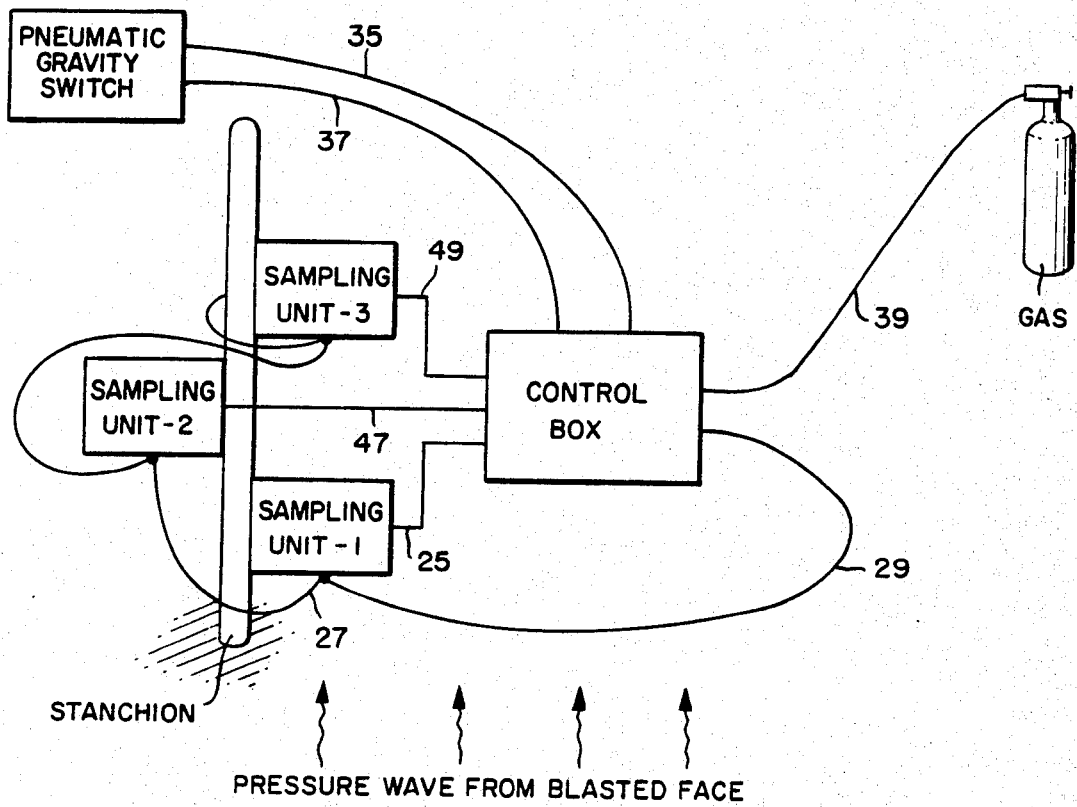
FIG. 1 schematically depicts the major component elements used to operate our invention.

The basic components of the preferred embodiment of our invention are shown in FIG. 1. These components are the sampling unit(s), the pneumatic gravity actuated switch, the control box with its connections, and the gas supply. Each of these is schematically shown in FIG. 1 and how they would be connected to each other in an underground mine. Initially, a pressure wave from the blast rotates a vane which in turn activates a pneumatic response from a gravity switch. This switch in turn triggers a timing sequence in the control box. Once activated, the control box sends pneumatic signals at preset time intervals through the control signal conduits to air solenoids in the sampling units (three shown). Each sampling unit has its own conduit connected to the control box and its own associated air solenoid. The solenoids in the representative sampling units activate pistons in the sampling units. Sequentially, the pistons open a valve in the sampling unit which releases a liquid previously placed therein from the bottom of the unit. After the environmental mine gas enters the sampling unit through the same hole discharging the liquid, the control signals sequentially closes the valve in the sampling unit to seal in the representative environmental gas sample for a specific time and mine location. This captured gas sample is retrieved at a later time, when mine conditions are deemed safe. A stanchion which extends up from the mine floor vertically supports the sampling unit assembly and the pneumatic gravity switch.

FIG. 2 depicts one of the sampling unit assemblies and gravity switch and its associated air vane previously referred to in FIG. 1. Each sampling unit assembly is identical in structure and operation, consequently, only one will be described in detail, it being understood that the others are structurally and functionally the same. Both the sampling unit and the gravity switch are rigidly held to the support stanchion 1 by their U-shaped bracket assemblies 3 and 5, respectively. The sampling unit assembly is made of its sampling container 7, the sampling valve 9, the hand-operated lever 11 connected to a ball valve (not shown) within the container, the actuator 13, the horizontal support 15 for the foregoing, the air solenoid 17, the fluid conduits 19 and 21 from the solenoid to actuator, and the pneumatically operated valve 23. A hole in the bottom of container 7 allows the liquid originally placed therein (via upper valve 11) to be discharged to the floor and also allows the ambient gas to enter the container. Manually operated ball valve is normally placed by lever 11 in its closed position to retain the gas sample, except when the liquid is first placed in the container. Fluid conduit lines 25 connect the control box, whereas fluid conduits 27 and 29 connect the solenoid to a pressurized air supply. As indicated before, each solenoid has its own control signal line, like line 25, connected directly to the control box. Also each unit has an air supply line 27 which is initiated as the control box interconnects sampling units, and terminates at the last sampling unit (not shown in FIG. 2, see FIG. 1, Unit #3).

The gravity switch 31 and air vane 33 are also illustrated in FIG. 2. The fluid conduits 35 and 37 to and from the control box are shown. Line 35 supplies a pressurized gas to the gravity switch and the other line 37 sends an air signal to the control box when the movement limit is made by the vane 33. This air signal starts the timing sequence to be described hereinafter. As shown by the arrow, the air vane is rotably mounted to its associated switch such that the blast wave rotates it counterclockwise until it reaches the referred to movement limit—shown in dotted line format.

Fluid conduit lines 19 and 21 interconnect each solenoid to each of its associated actuators as shown in FIG. 2. Line 19 supplies a normally pressurized source of gas which keeps the valve 23 in a closed position. When a source of pressurized gas supplied by line 19 is lessened or depressurized, line 21 supplies a pressurized gas to a piston (not shown) in actuator 13 in response to the solenoid's movement. A signal from the control box initiates this action which results in the pneumatically operated valve 23 being opened by the gas as it moves the piston and associated linkage. Valve 23 remains open as long as the control box signal is supplied to the solenoid. Once the signal ceases, the pressurized gas is again supplied, via line 19, to closed valve 23 and keeps it closed.

The power to provide the necessary signals to cause the movement in the gravity switch solenoid and the sampling unit assembly comes from a source of pressurized gas, like $N_2$ or air (see FIG. 1) connected by a conduit 39 to the control box. Appropriate conduits, as described with respect to FIG. 2, connect the control box to each of the sampling unit assemblies and the gravity switch. In turn the sampling units are also serially connected to each other (see FIG. 1) by conduits. The valve 23 in the sampling unit is actuated and a liquid previously placed in container 7 thereabove is gravity released. As the liquid leaves the container, ambient gas replaces it via its opened bottom hole. Following this movement of gas, a signal from the control box stops, causing the solenoid to shift the pressurized gas from one line 19 to the other 21. This returns the actuator's piston to its original position which closes the valve 23 via link connection 41 sealing the air sample within the container. Before this occurs, the hand-operated level 11 has been rotated to move an inner ball valve to its closed position. The actual retrieval of the captured gas sample is accomplished by rotating the knob of normally closed sampling valve 9 after a container (not shown) with a needle valve is inserted in outlet 43. The container is subject to a vacuum pressure to insure the movement of the gas sample thereinto.

Figure 3:
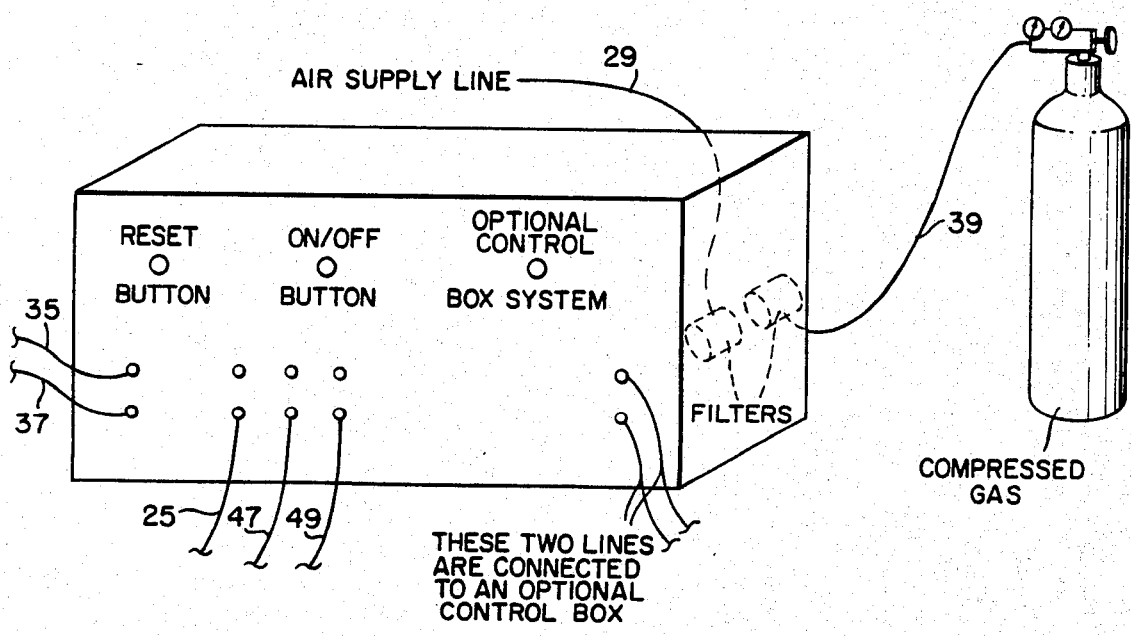
FIG. 3 shows the control box of FIG. 1 and its associated conduits and gas source.

FIG. 3 shows the control box of FIG. 1, its connected conduits, the pressurized gas power source used to move the solenoids, gravity switch, piston, valve 23, etc. After the blast wave moves the vane 33, the switch 31 sends a signal to the control box. The control box is an off-the-shelf unit and functions to send signals to release the liquids in the sample containers and, after a time delay, close valve 23 to seal the gas sample in the container. By using different settings for on delay and for off delay times for each sampling unit assembly, the time their respective gases are captured can be regulated. One of the pneumatic control sequence boxes we have employed is Model #22NCSB102 made by the Numatrol Company of Highland, Mich. 48031. Normally, the time intervals involved are just seconds from the initial mine blast before the liquids are released, with the sampling unit 23 closing just seconds thereafter to capture the ambient gas. For example, each of the sampling units could sample gases at two minute consecutive intervals when the air movement in the face area is low (less than 100 feet per minute). At higher air velocities, the time intervals would be correspondently shorter.

Again, referring to FIG. 3, there is shown a series of gascarrying conduits 25, 27, 29. One of each of these conduits is connected to each of the three sampling units. The conduit 35 and 37 go to the gravity switch and the air supply conduit 29 supplies pressurized gas serially to each of the sampling unit assemblies via its respective solenoid as in FIG. 2.

It should be apparent that changes can be made to many aspects of the preferred embodiment while still using the principles behind our invention. The number of sampling unit assemblies, solenoids, switches, vanes, and conduits can vary as well as their specific construction. What cannot vary is the construction of a pneumatically operated gas sample unit activated by a blast which employs no electrical or other potential sources of ignition in its operation. None of the variates should be used to change the scope and spirit of our invention which is to be limited only by the claims that follow.

We claim:

1. A blast activated gas sampling system for use in an underground mine comprising:
   a blast activated switch means for receiving and being responsive to a blast whose gas is to thereafter be sampled;
   a pneumatically operated sample unit assembly to retain the ambient gas after the switch activating blast occurs;
   a pneumatically operated control means for controlling the operation of the sample assembly by sending pneumatic signals to said sample unit assembly at preselected time intervals, said control means being operatively connected to said switch for its initial activation, and said sample unit assembly to control the gas sample collection timing; and
   a source of pressurized gas in fluid communication with said control means to provide the power for its operation.

2. The gas sampling system of claim 1 wherein said switch means comprises a gravity actuated switch and a movable vane attached together, said vane being movable by the pressure wave from the blast to activate the switch.

3. The gas sampling system of claim 2 wherein said sample unit assembly comprises a pneumatically operated solenoid, a gas container, and a valve for the container responsive to the operation of the solenoid to retain a gas sample therein.

4. The gas sampling system of claim 3 wherein said container has additional means attached to it to provide for the placement and retaining of a liquid, and the release of the retained gas sample therefrom.

5. The gas sampling system of claim 3 wherein said gas sample unit assembly also comprises a pneumatically operated piston connected to said valve and actuated by the solenoid through fluid conduits attached thereto.

* * * * *